(12) United States Patent
Mueller

(10) Patent No.: US 9,447,947 B2
(45) Date of Patent: Sep. 20, 2016

(54) ILLUMINATION DEVICE HAVING PRIMARY LIGHT UNIT AND PHOSPHOR ELEMENT

(71) Applicant: OSRAM GmbH, Munich (DE)

(72) Inventor: Juergen Mueller, Berlin (DE)

(73) Assignee: OSRAM GMBH, Munich (DE)

( * ) Notice: Subject to any disclaimer, the term of this patent is extended or adjusted under 35 U.S.C. 154(b) by 0 days.

(21) Appl. No.: 14/559,949

(22) Filed: Dec. 4, 2014

(65) Prior Publication Data

US 2015/0204519 A1    Jul. 23, 2015

(30) Foreign Application Priority Data

Jan. 20, 2014   (DE) .................. 10 2014 200 937

(51) Int. Cl.

| | | |
|---|---|---|
| *F21V 1/00* | (2006.01) | |
| *F21V 21/00* | (2006.01) | |
| *F21V 9/16* | (2006.01) | |
| *F21V 14/08* | (2006.01) | |
| *F21V 9/08* | (2006.01) | |
| *F21V 13/02* | (2006.01) | |
| *F21V 13/14* | (2006.01) | |
| *G03B 21/20* | (2006.01) | |
| *A61B 1/06* | (2006.01) | |
| *F21Y 101/02* | (2006.01) | |

(52) U.S. Cl.
CPC ............... *F21V 14/08* (2013.01); *A61B 1/063* (2013.01); *A61B 1/0653* (2013.01); *A61B 1/0684* (2013.01); *F21V 9/08* (2013.01); *F21V 9/16* (2013.01); *F21V 13/02* (2013.01); *F21V 13/14* (2013.01); *G03B 21/204* (2013.01); *F21Y 2101/025* (2013.01)

(58) Field of Classification Search
CPC ............ F21V 14/08; F21V 9/16; F21V 9/08; F21V 13/02; F21V 13/14; H04N 9/00; A61B 1/00; G03B 21/204; F21Y 2101/025
See application file for complete search history.

(56) References Cited

U.S. PATENT DOCUMENTS

2011/0310363 A1* 12/2011 Kita ................... G03B 21/204
                                                       353/98
2012/0026472 A1    2/2012 Masuda
(Continued)

FOREIGN PATENT DOCUMENTS

DE        102012211837 A1    1/2014

OTHER PUBLICATIONS

German Office Action issued Sep. 30, 2014 for German Patent Application No. 102014200937.5 filed Jan. 20, 2014, 7 pages.

*Primary Examiner* — Donald Raleigh
(74) *Attorney, Agent, or Firm* — Viering, Jentschura & Partner mbB

(57) ABSTRACT

An illumination device includes a primary light unit for the emission of primary light, a phosphor element for the conversion of an excitation light part of the primary light and as a result the emission of conversion light, and a coupling element, to supply the excitation light part of the primary light to the phosphor element. The element has a first conversion region, which is configured to emit a first conversion light, and a second conversion region, which is configured to emit a second conversion light, which differs in its spectral properties from the first conversion light. The primary light unit, the element, and the coupling element are arranged such that in operation, the excitation light part is supplied to the phosphor element via the coupling element, wherein simultaneously a useful light part of the primary light is also supplied, guided via the coupling element, conversion-free to an illumination application.

19 Claims, 3 Drawing Sheets

(56) References Cited

U.S. PATENT DOCUMENTS

2012/0201030 A1* 8/2012 Yuan .................... G02B 26/008
            362/293

2012/0316397 A1  12/2012 Berben et al.
2013/0278902 A1* 10/2013 Chen .................... G03B 21/204
            353/31

* cited by examiner

ILLUMINATION DEVICE HAVING PRIMARY LIGHT UNIT AND PHOSPHOR ELEMENT

CROSS-REFERENCE TO RELATED APPLICATION

This application claims priority to German Patent Application Serial No. 10 2014 200 937.5, which was filed Jan. 20, 2014, and is incorporated herein by reference in its entirety.

TECHNICAL FIELD

Various embodiments relate generally to an illumination device having a primary light unit for the emission of primary light usable as excitation light and a phosphor element for the conversion of the excitation light.

BACKGROUND

Although presently gas discharge lamps are still often used as light sources of high luminance, more recent developments are moving toward combining a primary light unit of high power density, for example, a laser, with a phosphor element arranged spaced apart thereto. The phosphor element converts the excitation light of the primary light unit and in turn emits a conversion light of longer wavelength. Such a remote phosphor arrangement can be used, for example, as a light source of a projection device, which illustrates a possible area of use, but is not to restrict the subject matter of the invention in its generality.

SUMMARY

An illumination device includes a primary light unit for the emission of primary light, a phosphor element for the conversion of an excitation light part of the primary light and as a result the emission of conversion light, and a coupling element, to supply the excitation light part of the primary light to the phosphor element. The element has a first conversion region, which is configured to emit a first conversion light, and a second conversion region, which is configured to emit a second conversion light, which differs in its spectral properties from the first conversion light. The primary light unit, the element, and the coupling element are arranged such that in operation, the excitation light part is supplied to the phosphor element via the coupling element, wherein simultaneously a useful light part of the primary light is also supplied, guided via the coupling element, conversion-free to an illumination application.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1:
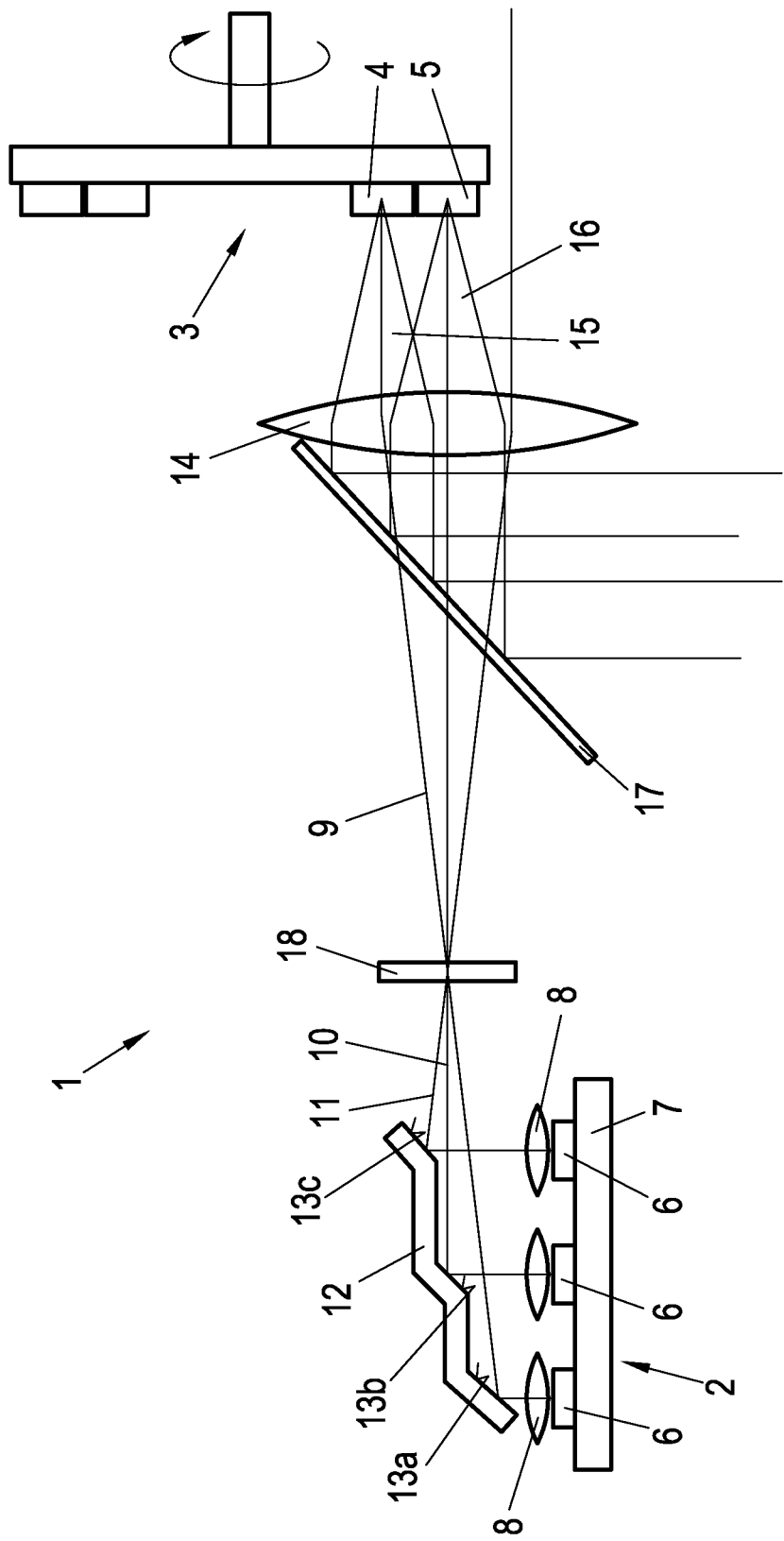
FIG. 1 shows a first embodiment having a reflection element for the relative tilting of the beam bundles emitted from the primary light unit.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

Various embodiments specify an illumination device, which provides additional effects in relation to the prior art, having primary light unit and phosphor element.

Various embodiments provide an illumination device having a primary light unit for the emission of primary light in operation, a phosphor element for the conversion, e.g. full conversion, of an excitation light part of the primary light and as a result thereof emission of conversion light, and a coupling element, to supply the excitation light part of the primary light to the phosphor element, wherein the phosphor element has a first conversion region, which is designed for the emission of first conversion light, and has a second conversion region, which is designed for the emission of second conversion light, which differs in its spectral properties from the first conversion light. Furthermore, the primary light unit, the phosphor element, and the coupling element are arranged such that in operation, the excitation light part is supplied to the phosphor element via the coupling element, wherein simultaneously a useful light part of the primary light is also supplied, guided via the coupling element, conversion-free to an illumination application.

Various embodiments are found in the following description and in the dependent claims, wherein the description does not always differentiate in detail between device aspects and method aspects or use aspects; however, the disclosure is always implicitly to be read with regard to all claim categories.

According to the various embodiments, the primary light emitted from the primary light unit is thus not only used as the excitation light for illuminating the phosphor element, but rather simultaneously, i.e., at the same point in time, a part of the primary light is provided conversion-free to the illumination application; this applies in operation e.g. for at least 80%, e.g. at least 90%, and e.g. 100% of the operating duration (activation duration) of the illumination unit.

The excitation light part and the useful light part may be at least independent from one another insofar as they at most jointly increase or decrease (with the same sign), but one does not increase when the other decreases (or vice versa). The excitation light part and the useful light part should thus behave at most directly proportionally to one another—for example, if a single primary light source is provided and the light thereof is divided into an excitation light beam bundle and a useful light beam bundle, both beam bundles are affected (with the same sign) by an adaptation of the output power. The excitation light part and the useful light part are e.g. completely independent from one another, i.e., a separate primary light unit is provided in each case (see below in detail).

"Conversion-free" means without a change of the spectral properties by a phosphor element. The useful light component at the output of the illumination device, i.e., where the light is provided to the illumination application, may have a spectrum which is substantially congruent with that of the primary light unit directly downstream, for example, at least 90%, 95%, or 98%, respectively; for example, no filters are thus e.g. also arranged in the beam path.

The conversion-free primary light "supplied to the application" is available at an output of the illumination device and is also used correspondingly in the uses according to various embodiments (conversion-free) for illumination, for example, in a projection device, for operating area illumination, and/or as a light source of an endoscope for industrial or medical purposes. The illumination unit can offer special advantages insofar as it can provide three colors simultaneously; accordingly, it can be used, for example, as a light source in a 3-LCD projection or also 3-DMD projection. Although ultraviolet primary light is generally also conceivable, this may relate to blue primary light and one color channel is available at the output.

The phosphor element has at least two conversion regions, which differ with regard to the spectral properties of the respective emitted conversion light. In various embodiments, the first conversion light is red light and/or the second conversion light is green light, i.e., two color channels are e.g. available with first and second conversion lights. An interaction can now result insofar as the illumination device according to various embodiments can then be used with e.g. the blue primary light as an RGB module.

The conversion light is also supplied to the illumination application, wherein it can also firstly be adapted in its spectral properties, for example, i.e., only a component of the illumination can then also be available (a part of the spectrum can be filtered out, for example). The first and the second conversion lights (and if present also a further conversion light) may be separately supplied as individual channels to the illumination, i.e., not as mixed light.

In this case, the various channels share the same coupling element, which is used in each case for the beam shaping, which may help to reduce the number of the individual parts to be installed and therefore to be handled in the production. As will become clear hereafter in detail, the coupling element may be a monolithic part, i.e., a part made of "one casting" without material boundaries therein, e.g. a comparatively simply constructed focusing lens, which is available with high precision, however.

Insofar as reference is made to "red" (R), "green" (G), or "blue" (B) light, respectively, this can mean, for example, in the CIE standard color system (CIE 1931, DIN 5033) a region spanned around a respective color point with $\Delta x=+/-0.2, +/-0.1$, or $+/-0.05$ and (independently thereof) $\Delta y=+/-0.2, +/-0.1$, or $+/-0.05$, respectively, in each case increasingly e.g. in the sequence they are mentioned. The respective "color points" are preferably at $(x=0.64)/(y=0.33)$ (R), $(x=0.3)/(y=0.6)$ (G), and $(x=0.15)/(y=0.06)$ (B). Light which differs "in its spectral properties" may be to be read according to this definition as red and green light; the primary light is e.g. accordingly blue light.

Insofar as reference is made to the emission, propagation, and conversion of light, this is not to imply, of course, that one of these must take place to fulfill the subject matter; an illumination device is described (neglecting uses/methods), which is designed accordingly so that emission/propagation/conversion should thus take place "in operation" of the illumination device.

With regard to a weighting between excitation light component and useful light component, it may be for the first (the excitation light part) to make up at least 50%, e.g. at least 60% or 70%, and (independently of the lower limit) at most 95%, e.g. at most 90%, 85%, or 80%, respectively, of the primary light.

In various embodiments, the primary light unit has a plurality of primary light sources, namely in each case at least one separate primary light source for the excitation light part and the useful light part, which thus each only relates to the respective light part.

In general, a LASER may be provided as the primary light source and accordingly a plurality of LASER light sources are e.g. provided; a laser diode source is preferred as the LASER light source, a plurality of laser diode sources may thus be provided. In various embodiments, it may be provided that in each case at least one laser diode source is provided for the first and second conversion regions and the useful light component. The light of all primary light sources is guided in this case via the shared coupling element.

A "laser diode source" can also be constructed per se from a plurality of laser diodes (in the simplest case, however, also from only a single one), the laser light of which is combined using an optic and which are housed jointly, for example (multi-die package); the laser diodes can be arranged in this case in the form of an array or also a matrix. The laser diodes of the laser diode source can be activatable, for example, as a unit, i.e., not independently of one another.

Although in general primary light sources could also be provided for the primary light unit, the respective emitted primary light of which differs in its spectral properties, i.e., for example, a UV primary light source and a blue primary light source, the primary light of the individual primary light sources preferably has the same spectral properties. Blue primary light sources may exclusively be provided.

The plurality of primary light sources of the primary light unit may be structurally identical to one another, which can simplify the integration. Expressed in general words, a "primary light source" can be viewed, for example, as an integral component activatable as a unit, on the e.g. precisely one light exit surface of which LASER light is emitted.

various embodiments, in each case a separate beam bundle is provided for the illumination of the first and second conversion regions and for the conversion-free output, these beam bundles at most being coincident sectionally with the respective other beam bundles in relation to the respective primary light propagation direction. In other words, the beam bundles can intersect, for example (and preferably also do so, cf. the embodiments), but they propagate separately from one another e.g. over long routes, for example, e.g. in this sequence over at least 50%, 70%, or 90%, respectively, of the route taken along the respective beam bundle (in the primary light propagation direction) between a light exit surface of the primary light source and the phosphor element. Over a respective route, the beam bundles are to be spaced apart from one another in a plane perpendicular to the primary light propagation direction of one of the beam bundles, thus, they do not overlap or they do not touch one another, respectively.

For the sake of completeness, it is to be noted that the idea of various embodiments does not require such spaced apart beam bundles in its generality; for example, a single (continuous) excitation light beam bundle could also illuminate the various conversion regions. However, the division into beam bundles may be provided, wherein e.g. each beam bundle is emitted from a separate primary light source, which can also be adjustable in its power independently of the others, for example. One laser diode source may be provided in each case for each beam bundle.

The beam bundles, at least the first and the second, e.g. also the third, are each collimated per se in an embodiment when they are incident on the coupling element. Thus, beam bundles which are parallel per se are incident on the coupling element, and the first and the second beam bundles (and optionally further beam bundles oriented on the phosphor element) thereof are each focused per se on the phosphor element, specifically the first beam bundle is focused on the first conversion region and the second on the second.

The beam bundles are thus e.g. incident, each collimated per se, on the coupling element, but they are e.g. tilted in relation to one another; they are collimated in relation to one another by the coupling element (they are thus then parallel to one another) and are focused on the phosphor element.

Two beam bundles "tilted in relation to one another" can, for example, enclose an angle of at least 5°, 10°, 15°, 20°, or 25° with one another, wherein possible upper limits are at 60°, 50°, or 40°, respectively, for example. In the case of at least three beam bundles, the tilt angle is considered in relation to the respective other beam bundles (and it is e.g. to have a corresponding value) in this case for each of the beam bundles.

Although a corresponding beam path could also be implemented in general using a coupling element penetrated by the beam bundles, the light entry and/or exit surface(s) of which were adapted accordingly as freeform surface(s), for example, in a computer-assisted optimization method, a focusing lens may be provided as a coupling element. The beam bundles tilted in relation to one another are thus, directly upstream from the focusing lens, also tilted in relation to its optical axis (possibly neglecting a beam bundle parallel to the optical axis) and, directly downstream from the focusing lens, are parallel to one another and preferably also to the optical axis of the focusing lens. The focusing lens may be a biconvex lens.

Using the above-described beam guiding, a coupling element (the focusing lens), which is comparatively simple with regard to its construction, may thus be provided, which can thus be available cost-effectively as a standard component, on the one hand, but also simultaneously with high precision.

To tilt the beam bundles in relation to one another, in various embodiments, a reflection element can be provided upstream from the coupling element, the reflection surface of which is constructed from reflection surface regions tilted in relation to one another. The beam bundles may be incident collimated in relation to one another on the reflection element, and are specifically each incident on a different reflection surface region; they are thus reflected and tilted in relation to one another at the same time.

The reflection surface regions do not necessarily have to be subregions of a coherent reflection surface, but may be to be fixed in their relative position and relative tilt. The reflection surface regions may be each planar per se, wherein then the angle tilt between the surface normals of closest-adjacent reflection surface regions can be, for example, at least 5°, 10°, or 15°. In the case of reflection surface regions which are not planar per se, the relative tilt of the beam bundles of the reflection surface immediately upstream and downstream can be compared in each case to ascertain the tilt thereof.

For example, a simple, correspondingly segmented deflection mirror can be provided as a reflection element; however, a stepped mirror is also possible, using which, in addition to a tilt of the beam bundles, the distance thereof perpendicular to the primary light propagation direction can also be adapted in the case of beam bundles collimated in relation to one another. Thus, for example, the distance between the beam bundles can be reduced, to be able to illuminate conversion regions arranged closer to one another, in spite of a respective component-related minimum distance between the primary light sources, in contrast.

A similar adaptation of the distance of the beam bundles can also be performed using a lens system, for example, a combination of a scattering lens and a focusing lens upstream therefrom in relation to the primary light.

The reflection element can also be provided in an embodiment as a component reflection element, which means a reflection element transmissive for the conversion light, but reflective for the primary light. This component reflection element, for example, a dichroic mirror, is arranged in this case in the beam path such that the primary light is reflected in the above-described manner and the conversion light generated as a result thereof is transmitted. "Transmission"/ "reflection" can in general mean in the scope of this disclosure that the degree of transmission/reflection is, for example, to be at least 80%, e.g. at least 90%, or 95%, in relation to the respective light under discussion.

In various embodiments, the phosphor element is operated in reflection (which may also generally be independently thereof), i.e., the excitation light falls in one direction on the phosphor element and the conversion light emitted therefrom in the direction opposite thereto is used. For efficiency reasons, in this case the rear side of the phosphor element opposite (to the excitation light incidence side) can be, for example, mirrored and/or provided with a cooling body, e.g. a cooling body having mirrored surface.

In general, the phosphor element may be a one-piece part, the various conversion regions are thus applied, for example, to the same base body. Thus, a first phosphor, for example, also a phosphor mixture having a first phosphor and further phosphors, can be applied as the first conversion region, and a second phosphor can be applied as the second conversion region to the shared base body. The first and second conversion regions are to differ in at least one phosphor in the case of a phosphor mixture/phosphor mixtures, e.g. in all phosphors (i.e., no phosphor is found simultaneously in the first and the second conversion regions). It may also be for manufacturing reasons that the conversion regions do not directly adjoin one another, but rather are spaced apart somewhat from one another.

In various embodiments, a red phosphor/a red phosphor mixture forms the first conversion region and a green phosphor/a green phosphor mixture forms the second conversion region. For example, europium-doped $CaSrSi_5N_8$ and/or europium-doped $CaAlSiN_3$ can be provided as the red phosphor (mixture). For example, cerium-doped YAG phosphors can be provided as the green phosphor (mixture), for example, $YAG:Ce(Y_{0.96}Ce_{0.04})_3Al_{3.75}Ga_{1.25}O_{12}$.

In addition to the first and second conversion regions, further conversion regions can also be provided (which each differ from the others in their spectral properties), i.e., more primary colors can be available; for example, a third conversion region can be provided, the third conversion light of which differs from the first and second conversion lights. A yellow phosphor/a yellow phosphor mixture may form the third conversion region. For example, cerium-doped YAG (Ce:YAG) or also a mixture of a yellow phosphor (Ce:YAG) and a green phosphor (Ce:LuAG) can be provided as the yellow phosphor (mixture).

The phosphor element can also be provided as a phosphor wheel in various embodiments, i.e., mounted so it is rotatable about an axis of rotation. The conversion regions can be arranged successively in the radial direction in this case, for example, as interleaved ring segments, e.g. as interleaved rings, i.e., circumferentially in each case. Only one portion or subsection of a respective conversion region is then illuminated in each case and it is continuously changed by rotation of the phosphor wheel, for example, which may be provided for thermal reasons (the phosphor which is presently not illuminated can cool down somewhat).

An interaction can result insofar as the conversion regions are illuminated in parallel according to various embodiments, so that ideally each conversion region can be provided about the entire circumference on a phosphor wheel; in comparison to alternating successive conversion regions in the circumferential direction (of the phosphor wheel), the route used for the cooling can be enlarged.

For the useful light part, a window transmissive for the primary light can also be provided in the phosphor element, e.g. in a phosphor wheel, for example, also a through hole (without material therein). On the other hand, the useful light part can also, for example, be reflected in an oriented manner from the phosphor element, i.e., a mirror can be applied. In both cases, a corresponding region can be provided in a ring shape (radially interleaved with the conversion regions) on a phosphor wheel, i.e., accordingly a transmissive or reflective region. On the other hand, the useful light part can also be guided past the phosphor element.

In addition to the already described possibilities for tilting the beam bundles in relation to one another, in various embodiments, a transmission element having a light entry surface and a light exit surface can be provided, and at least one of these light passage surfaces is provided made of light passage surface regions tilted in relation to one another, i.e., in segmented form. This transmission element is then arranged in the beam path such that the beam bundles pass through different light passage surface regions, e.g. in each case precisely one beam bundle through each light passage surface region, and are tilted in relation to one another at the same time. The beam bundles are thus tilted in relation to one another during the transition between two media of different indices of refraction (the surrounding medium is typically air and the transmission element has a greater index of refraction in relation thereto). The light exit surface of the transmission element may be segmented.

In various embodiments, the light passage surface regions are each planar per se, i.e., in each case light exit surface regions which are planar per se may thus be provided. With regard to an ascertainment of the tilt (between the surface normals in the case of planar surface regions, otherwise via the beam tilt) and preferred values for this purpose, reference is made to the above disclosure on the reflection surface regions.

At least one of the light passage surfaces of the transmission element can also be provided, for example, with a homogenization element, for example, an amorphous scattering element and/or a lens array. This can help, for example, to shape the respective illumination region of a beam bundle on the phosphor element as sharply delimited as possible, having a so-called top hat distribution.

In various embodiments, a wedge plate having segmented light exit surface is provided as the transmission element.

As already mentioned above, a phosphor element operated in reflection may be provided. In various embodiments, the coupling element is not only used in this case to guide the primary light in an above-described manner, but rather is additionally also used for guiding the conversion light, i.e., it supplies it to the illumination application. In this case, the coupling element can be closest adjacent to the phosphor element in relation to the beam path of the conversion light, so that no further optical element is thus arranged between coupling element and phosphor element in the beam path of the conversion light, i.e., the coupling element "collects" the conversion light. On the other hand, an optical element can also be interposed for this purpose, for example, a non-imaging optical element, e.g. a compound parabolic concentrator.

In various embodiments of the coupling element provided for guiding primary light and conversion light simultaneously, a decoupling component reflection element is provided downstream in relation to the conversion light (upstream in relation to the primary light), which is transmissive for the primary light, but reflective for the conversion light, for example, a dichroic mirror. It is arranged in the beam path such that the primary light is transmitted and the conversion light is reflected; the beam path of the conversion light is thus separated from that of the primary light.

In various embodiments, the decoupling component reflection element can have a plurality of decoupling reflection surfaces, specifically a first and a second decoupling reflection surface. The first decoupling reflection surface is transmissive for the primary light, but reflects the first conversion light; the second decoupling reflection surface is transmissive for the primary light and the first conversion light, but reflects the second conversion light. These decoupling reflection surfaces can be provided on a one-piece decoupling component reflection element, that is as various surfaces thereof; the decoupling component reflection element can also be embodied in multiple parts, however.

There are various possibilities with respect to the precise arrangement of the decoupling reflection surfaces, which relate to the first and the second conversion lights being emitted from various conversion regions and therefore spaced apart somewhat from one another. The first and the second conversion light beam bundles can in fact overlap, but the first and the second conversion light main beams, which are each formed as the mean value of the beams of the respective beam bundle weighted according to the power, are spaced apart from one another directly downstream from the phosphor element. The following considerations thus relate to the distance of first and second conversion light main beams directly downstream from the phosphor element, i.e., before influence is taken by an optical element.

The two decoupling reflection surfaces can now be spaced apart from one another enough, on the one hand (with respect to the conversion light route in between them), for example, by at least two times, four times, or six times the mentioned conversion light main beam distance, that a distance between first and second conversion light main beams directly downstream from the decoupling component reflection element is greater than directly downstream from the phosphor element; the first and the second conversion light beam bundles may thus be completely separated, i.e., they no longer overlap.

On the other hand, the distance between the decoupling reflection surfaces can also be selected to be relatively small, so that it corresponds to the mentioned conversion light main beam distance; the distance of the decoupling reflection surfaces may be selected so that the first and the second main beams are congruent directly downstream from the decoupling component reflection element, the first and second conversion lights are thus thoroughly mixed.

Also independently of an embodiment having two decoupling reflection surfaces, the decoupling component reflection element can be provided in various embodiments such that it reflects conversion light of a first polarization, but transmits conversion light of a second polarization (this can relate to the first and/or second conversion light). The conversion light of one of the two polarizations can then be guided, for example, by a mirror, back to the phosphor element, to be incident thereon again on the decoupling component reflection element after a scattering process, if necessary with another polarization.

The component of the light having the desired polarization may correspondingly be increased. Thus, for example, p-polarized conversion light can be decoupled and s-polarized conversion light would be guided back to the phosphor element, in order, after a scattering process thereon and therefore possibly being repolarized, to be incident again on the decoupling component reflection element (and to be decoupled in the case of a p-polarization).

The light may be transmitted with undesired polarization, to be incident again (in the opposite direction) on the decoupling component reflection element after a reflection on a reflection surface, and thus to be guided to the phosphor element along the same beam path as the conversion light, which was emitted from the phosphor element but heretofore was not yet incident on the decoupling component reflection element, but also in the opposite direction thereto.

A corresponding polarization-dependent decoupling can be of interest, for example, when a liquid crystal display screen is through-illuminated using the light generated by the illumination device. The suitable polarization can thus already be made available.

In general, the first and second conversion lights can each be comparatively broadband and the illumination application can then in each case only be supplied a narrowband component/narrowband components.

For example, for a 3D color space, in each case two narrowband components, for example, can also be cut out of the first and the second (and optionally a further) conversion light; the illumination would be supplied a first and a second component, which are each narrowband per se, from the first conversion light; this also applies for the second (and possibly further) conversion light. Depending on the conversion light, the narrowband components can be spaced apart not more than a few tens of nanometers from one another, for example.

For a 3D application, the narrowband components are then separated, i.e., made available as separate channels in each case, i.e., each decoupled separately. "Filtering out" of the narrowband components can be performed simultaneously with decoupling, for example, in that a corresponding narrowband decoupling component reflection element is provided, i.e., for example, a narrowband dichroic mirror, which reflects a first narrowband component of the respective conversion light out of the remaining beam path. Using a second narrowband dichroic mirror, the second narrowband component could then be reflected downstream from the first mirror out of the corresponding conversion light. Using the structure according to various embodiments, the components may then be available simultaneously, which can be of interest, for example, in the case of a 3D-LCD projector.

As already mentioned at the outset, various embodiments also relate to a use in which the excitation light part is incident on the phosphor element and simultaneously the useful light part is made available for illumination. At an output of the illumination device, the useful light part is thus emitted conversion-free and simultaneously, i.e., at the same point in time, the conversion light is emitted at (at least) one further output. Three outputs, i.e., a separate output in each case for the first and second conversion lights and the useful light part of the primary light, may be provided, wherein light is emitted simultaneously at the outputs (which is moreover also to be disclosed with regard to the device).

FIG. 1 shows an illumination device 1 according to various embodiments having a primary light unit 2 and a phosphor element 3. The phosphor element 3 has a first conversion region 4 for the emission of red light and a second conversion region 5 for the emission of green light, in each case upon illumination using the excitation light emitted from the primary light unit 2.

According to various embodiments, however, not only are two conversion regions 4, 5, which differ with regard to the spectral properties of the respective emitted conversion light, illuminated using the primary light unit 2, but rather useful light is made available simultaneously in a conversion-free manner.

The primary light unit 2 is equipped with three structurally identical laser diodes 6, which are mounted on a shared carrier 7. The laser diodes 6 emit blue laser light, wherein the beam bundle of the laser diode 6 respectively emitted from each laser diode 6 is collimated directly downstream using a respective collimation lens 8. The first beam bundle 9, the second beam bundle 10, and the third beam bundle 11 are then thus each collimated per se.

The primary light is then reflected on a reflection element 12, which has three reflection surface regions 13 tilted in relation to one another. The reflection element 12 is a stepped mirror, the reflection surface regions 13 are thus offset in relation to one another; in addition, they are also tilted, i.e., normals on the reflection surface regions 13 are thus not parallel to one another. As a result, the beam bundles 9, 10, 11, which are not only parallel per se, but rather also parallel to one another upstream from the reflection element 12, are tilted in relation to one another upon the reflection.

The beam bundles 9, 10, 11 are incident accordingly (tilted in relation to one another, each collimated per se) on the coupling element 14, namely a focusing lens arranged in the beam path.

The coupling element 14 collimates the beam bundles 9, 10, 11 in relation to one another and at the same time focuses each of them per se. Downstream from the coupling element 14, the beam bundles 9, 10, 11 are parallel to one another (upon observation of a respective main beam formed as the mean value of the beams weighted according to the power); the first beam bundle 9 is focused on the first conversion region 4, the second beam bundle 10 is focused on the second conversion region 5, and the third beam bundle 11 is supplied conversion-free to an output as the useful light part.

The conversion light emitted in each case upon the excitation using excitation light from the conversion regions 4, 5 is then also guided via the coupling element 14 (in the direction opposite to the primary light). The coupling element 14 is thus used simultaneously for the excitation light coupling and the conversion light decoupling.

The first 15 and the second conversion light beam bundle 16 are incident (in relation to the conversion light) downstream from the coupling element 14 on a decoupling component reflection element 17, namely a dichroic mirror, which is transmissive for the primary light, but reflects the conversion light.

Correspondingly, the first 15 and the second conversion light beam bundle 16 are reflected out of the beam path, and light can thus be made available at two further outputs of the illumination device 1. Light is available at the three outputs, i.e., the one primary light useful light part output, and the two conversion light outputs, simultaneously (i.e., not only sequentially).

A homogenization element 18, specifically an amorphous scattering element, which helps to improve the uniformity of the radiation strength distributions of the respective beam bundles 9, 10, 11, is arranged in a point of intersection of the beam bundles 9, 10, 11 upstream from the coupling element 14 (in relation to the primary light) (however, the beam bundles 9, 10, 11 may each be collimated per se and tilted in relation to one another in an unchanged manner in this case).

The phosphor element 3 is provided as a phosphor wheel, which is thus mounted so it is rotatable about an axis of rotation (which lies in the plane of the drawing). The phosphor wheel is shown in a schematic section in the figure; in each case an upper and a lower part is thus visible of the respective ring-shaped first 4 and second conversion regions 5, wherein the lower part is illuminated with excitation light.

In this case, a europium-doped $CaSrSi_5N_8$ as the red phosphor forms the first conversion region 4 and a YAG: $Ce(Y_{0.96}Ce_{0.04})_3Al_{3.75}Ga_{1.25}O_{12}$ as the green phosphor forms the second conversion region 5.

Figure 2:
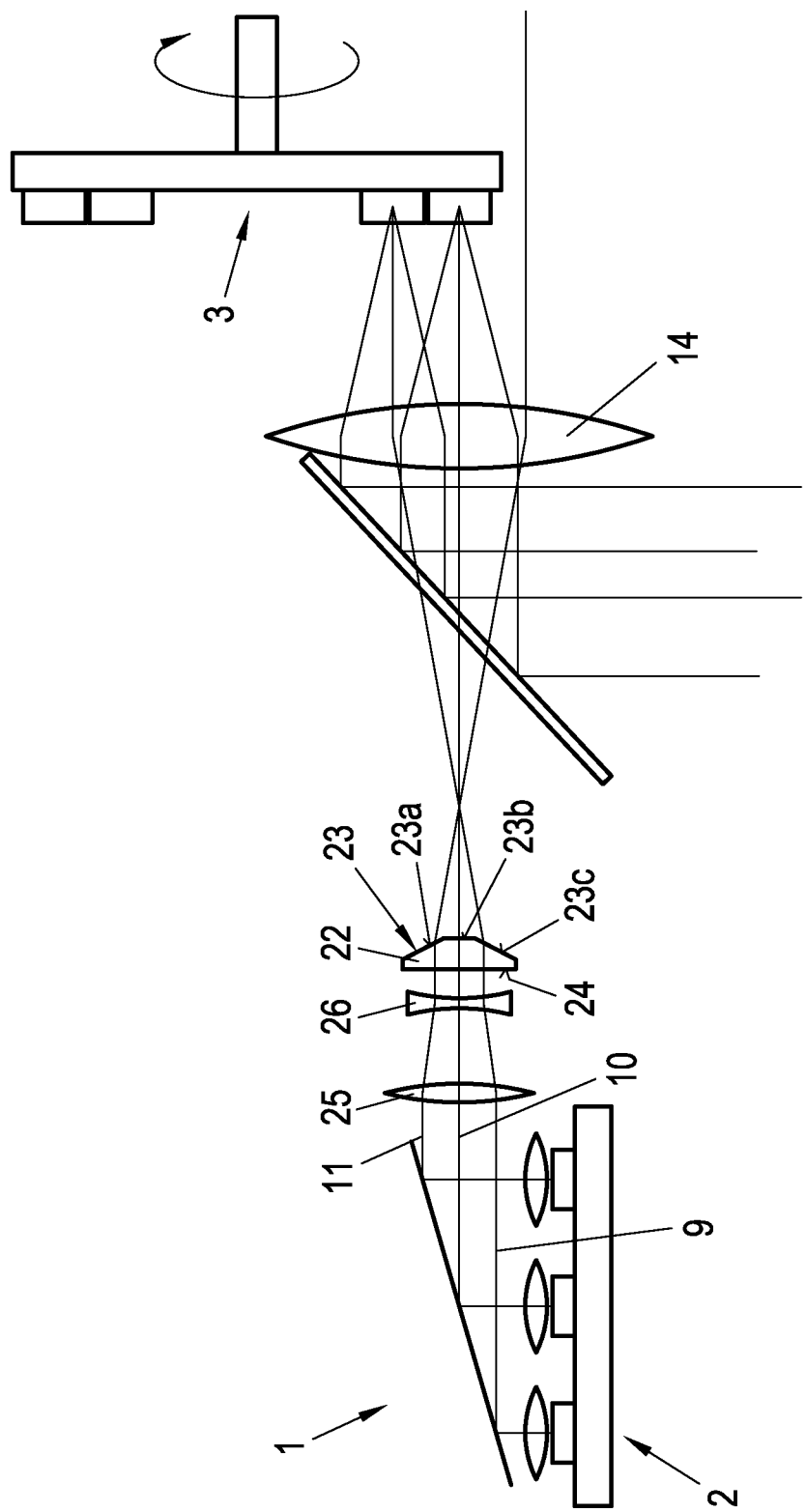
FIG. 2 shows a further embodiment, having a transmission element for the relative tilting of the beam bundles.

FIG. 2 shows a further illumination device 1 according to various embodiments, in which the primary light unit 2 and the phosphor element 3 of the lighting device 1 are constructed correspondingly according to FIG. 1. In general, parts which have the same function are specified using identical reference signs.

In this case, however, a stepped mirror having reflection surfaces 13 tilted in relation to one another is not provided for the relative tilting of the beam bundles 9, 10, 11, but rather a transmission element 22, the light exit surface 23 of which is constructed from light exit surface regions 23a, b, c tilted in relation to one another. The opposite light entry surface 24 is planar, and also the light exit surface regions 23a, b, c are each planar per se.

The beam bundles 9, 10, 11 are each collimated per se and also in relation to one another directly upstream from the transmission element 22. Using the light exit surface 23 constructed from light exit surface regions 23a,b,c, which are tilted in relation to one another, the beam bundles 9, 10, 11 are then refracted and at the same time tilted in relation to one another during the transition from the transmission element 22 made of quartz glass to the surrounding medium (air) having lower index of refraction.

The beam path which then follows corresponds to that according to FIG. 1, the beam bundles 9, 10, 11 are transmitted by the decoupling component reflection element 17 (the dichroic mirror) and parallelized in relation to one another by the coupling element 14 (the focusing lens) and at the same time each focused per se (in the case of the first 9 and second beam bundle 10) on the phosphor element 3; the third beam bundle 11 is again available conversion-free as a useful light component.

The decoupling of the conversion light also corresponds to the structure according to FIG. 1, and reference is made to the above statements.

In the embodiments according to FIG. 1, using the reflection element 12, i.e., the stepped mirror, not only the relative tilt of the beam bundles 9, 10, 11, but rather also their distance is adapted. For this purpose, in the embodiments according to FIG. 2, a lens system made of a focusing lens 25 and a scattering lens 26 is provided, wherein the focusing lens 25 is arranged upstream from the latter (with respect to the primary light) and the distance between the beam bundles 9, 10, 11 is reduced.

The scattering lens 26 then again collimates the beam bundles 9, 10, 11 in relation to one another, however, with a reduced distance perpendicular to the primary light propagation direction. A part-related greater distance between the laser diodes 6 can then accordingly be adapted, for example, to a comparatively small distance between the conversion regions 4, 5.

Figure 3:
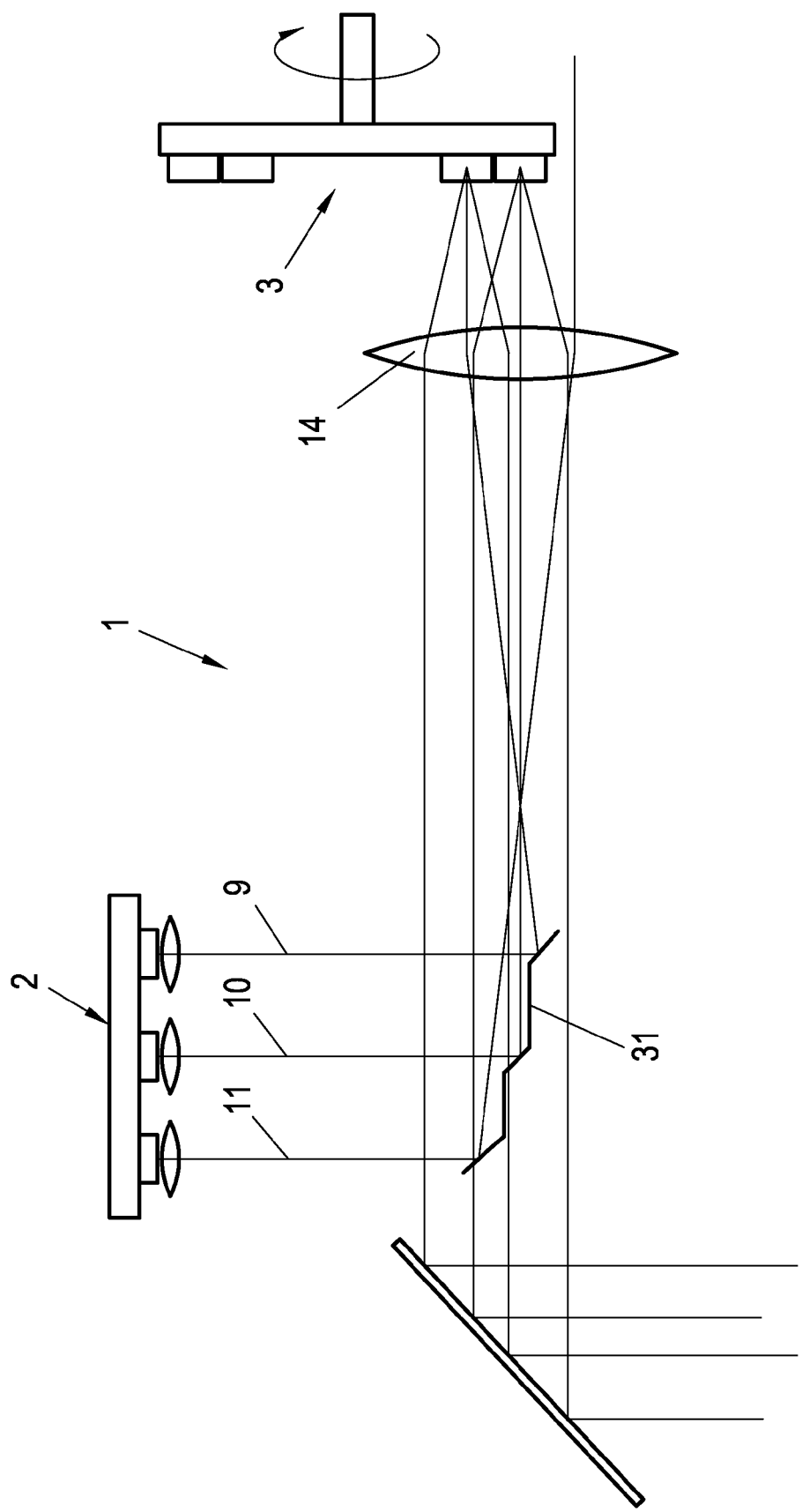
FIG. 3 shows an illumination device having a reflection element for the relative tilting of the beam bundles, which is transmissive for the conversion light, however.

FIG. 3 shows a third illumination device 1 according to various embodiments, the primary light unit 2 and phosphor element 3 of which are constructed corresponding to the preceding embodiments.

Furthermore, using the coupling element 2, beam bundles 9, 10, 11, which are tilted in relation to one another but are collimated per se, are collimated in relation to one another and (in the case of the excitation light component) focused on the phosphor element 3.

Similarly to the embodiment according to FIG. 1, the beam bundles 9, 10, 11 are also tilted in relation to one another (and adapted in their distance) using a reflection element, specifically a component reflection element 31, again a dichroic mirror, in the embodiment according to FIG. 3.

The component reflection element 31 is reflective for the primary light, but transmits the conversion light and can therefore be arranged in the beam path of the conversion light. Such an arrangement, in which the primary light coupling is thus arranged in the beam path of the conversion light and therefore "between" the conversion light outputs and the primary light useful light part output, can be of interest, for example, if outputs spatially spaced apart from one another as much as possible are desired with compact construction overall at the same time.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:
1. An illumination device, comprising:
a primary light unit for the emission of primary light in operation;
a phosphor element for the conversion of an excitation light part of the primary light and as a result the emission of conversion light; and
a coupling element, to supply the excitation light part of the primary light to the phosphor element;
wherein the phosphor element has a first conversion region, which is configured to emit a first conversion light, and a second conversion region, which is con- figured to emit a second conversion light, which differs in its spectral properties from the first conversion light, and wherein furthermore the primary light unit, the phosphor element, and the coupling element are arranged such that in operation, the excitation light part is supplied to the phosphor element via the coupling element, wherein simultaneously a useful light part of the primary light is also supplied, guided via the coupling element, conversion-free to an illumination application, wherein the primary light unit has a plurality of primary light sources, wherein in each case at least one separate primary light source is provided for the excitation light part and the useful light part, from which the respective other light part is independent in each case.

2. The illumination device of claim 1, wherein in operation the primary light propagates in the form of a plurality of at least sectionally non-coincident beam bundles, wherein, as the excitation light part, a first of the beam bundles is incident on the first conversion region of the phosphor element and a second of the beam bundles is incident on the second conversion region of the phosphor element, while in contrast, as the useful light part, a third of the beam bundles is supplied conversion-free to the illumination application.

3. The illumination device of claim 2, wherein the first and the second beam bundles are incident, each collimated per se, on the coupling element and are each focused per se thereby on the phosphor element.

4. The illumination device of claim 2, wherein the first and the second beam bundles are incident tilted in relation to one another on the coupling element and are collimated thereby in relation to one another.

5. The illumination device of claim 1, wherein the coupling element is a focusing lens.

6. The illumination device of claim 4, wherein a reflection element having a reflection surface made of reflection surface regions tilted in relation to one another is provided upstream from the coupling element with respect to the primary light and is arranged so that in operation, the beam bundles fall on different reflection surface regions, are reflected, and are tilted in relation to one another at the same time.

7. The illumination device of claim 6, wherein the phosphor element is operated in reflection and the coupling element, in addition to the supply of the excitation light, is provided for the purpose of guiding the conversion light away from the phosphor element and supplying it to the illumination application, wherein a component reflection element is provided as a reflection element, which is transmissive for the conversion light but reflective for the primary light, and wherein furthermore the component reflection element is arranged so that in operation, the conversion light passes through and the primary light is reflected.

8. The illumination device of claim 4, wherein a transmission element having light passage surfaces, specifically a light entry surface and a light exit surface, is provided upstream from the coupling element in relation to the primary light, wherein at least one of the light passage surfaces is provided made of light passage surface regions tilted in relation to one another and the transmission element is arranged such that in operation, the beam bundles pass through different light passage surface regions and are tilted in relation to one another at the same time.

9. The illumination device of claim 8, wherein the light passage surface regions of the transmission element are each planar per se.

10. The illumination device of claim 1, wherein the phosphor element is operated in reflection and the coupling element, in addition to the supply of the excitation light, is provided for the purpose of supplying the conversion light to the illumination application.

11. The illumination device of claim 10, wherein a decoupling component reflection element is provided downstream from the coupling element in relation to the conversion light, this reflection element being transmissive for the primary light, but being reflective for the conversion light, wherein the decoupling component reflection element is arranged so that in operation, the primary light passes through and the conversion light is reflected out of the beam path of the primary light.

12. The illumination device of claim 11, wherein the decoupling component reflection element has a first decoupling reflection surface, which is transmissive for the primary light, but is reflective for the conversion light, and a second decoupling reflection surface, which is transmissive for the primary light and the first conversion light, but is reflective for the second conversion light.

13. The illumination device of claim 11, wherein the decoupling component reflection element is implemented and arranged such that conversion light of a first polarization is reflected thereby, but conversion light of a second polarization is transmitted.

14. A method of operating an illumination device for illumination, the illumination device comprising:
a primary light unit comprising a plurality of primary light sources for the emission of primary light in operation;
a phosphor element for the conversion of an excitation light part of the primary light and as a result the emission of conversion light; and
a coupling element, to supply the excitation light part of the primary light to the phosphor element;
wherein the phosphor element has a first conversion region, which is configured to emit a first conversion light, and a second conversion region, which is configured to emit a second conversion light, which differs in its spectral properties from the first conversion light, and
wherein furthermore the primary light unit, the phosphor element, and the coupling element are arranged such that in operation, the excitation light part is supplied to the phosphor element via the coupling element, wherein simultaneously a useful light part of the primary light is also supplied, guided via the coupling element, conversion-free to an illumination application;

the method comprising:
providing at least one of said plurality of primary light sources for the excitation part;
providing at least a separate one of said plurality of primary light sources for the useful light part;
supplying the excitation light part of the primary light via the coupling element to the phosphor element; and simultaneously supplying the useful light part of the primary light also via the coupling element conversion-free to the illumination application.

15. An illumination device, comprising:
a primary light unit for the emission of primary light in operation;
a phosphor element for the conversion of an excitation light part of the primary light and as a result the emission of conversion light; and
a coupling element, to supply the excitation light part of the primary light to the phosphor element;
wherein the phosphor element has a first conversion region, which is configured to emit a first conversion light, and a second conversion region, which is configured to emit a second conversion light, which differs in its spectral properties from the first conversion light, and
wherein furthermore the primary light unit, the phosphor element, and the coupling element are arranged such that in operation, the excitation light part is supplied to the phosphor element via the coupling element, wherein simultaneously a useful light part of the primary light is also supplied, guided via the coupling element, conversion-free to an illumination application,
wherein in operation the primary light propagates in the form of a plurality of at least sectionally non-coincident beam bundles,
wherein, as the excitation light part, a first of the beam bundles is incident on the first conversion region of the phosphor element and a second of the beam bundles is incident on the second conversion region of the phosphor element, while in contrast, as the useful light part, a third of the beam bundles is supplied conversion-free to the illumination application,
wherein the first and the second beam bundles are incident tilted in relation to one another on the coupling element and are collimated thereby in relation to one another.

16. The illumination device of claim 15, wherein a reflection element having a reflection surface made of reflection surface regions tilted in relation to one another is provided upstream from the coupling element with respect to the primary light and is arranged so that in operation, the beam bundles fall on different reflection surface regions, are reflected, and are tilted in relation to one another at the same time.

17. The illumination device of claim 16, wherein the phosphor element is operated in reflection and the coupling element, in addition to the supply of the excitation light, is provided for the purpose of guiding the conversion light away from the phosphor element and supplying it to the illumination application, wherein a component reflection element is provided as a reflection element, which is transmissive for the conversion light but reflective for the primary light, and wherein furthermore the component reflection element is arranged so that in operation, the conversion light passes through and the primary light is reflected.

18. The illumination device of claim 15, wherein a transmission element having light passage surfaces, specifically a light entry surface and a light exit surface, is provided upstream from the coupling element in relation to the primary light, wherein at least one of the light passage surfaces is provided made of light passage surface regions tilted in relation to one another and the transmission element is arranged such that in operation, the beam bundles pass through different light passage surface regions and are tilted in relation to one another at the same time.

19. The illumination device of claim 18, wherein the light passage surface regions of the transmission element are each planar per se.

* * * * *